United States Patent [19]

Bloom et al.

[11] Patent Number: 4,909,242

[45] Date of Patent: Mar. 20, 1990

[54] EXPANDABLE CUFF ASSEMBLY FOR LAVAGE MACHINES

[75] Inventors: Devin A. Bloom, Phoenix; K. Tom Jones, Chandler, both of Ariz.

[73] Assignee: Pacific Bio Systems, Inc., Phoenix, Ariz.

[21] Appl. No.: 200,501

[22] Filed: May 31, 1988

[51] Int. Cl.⁴ .................... B08B 3/02; A61M 13/00
[52] U.S. Cl. .................................. 128/66; 422/28
[58] Field of Search ........... 604/23, 289, 293, 352; 128/65, 66, 202.12, 368, 370, 375; 134/34, 36, 42, 191, 199, 200; 422/28

[56] References Cited

U.S. PATENT DOCUMENTS

| | | | |
|---|---|---|---|
| 2,098,272 | 11/1937 | Benson | 128/375 |
| 2,248,205 | 7/1941 | Stobbe | 15/21 |
| 2,587,644 | 3/1952 | Newman | 128/66 |
| 2,785,824 | 3/1957 | Reeves | 220/46 |
| 3,103,016 | 9/1963 | Perlman | 2/270 |
| 3,178,779 | 4/1965 | Clark et al. | 20/69 |
| 3,266,657 | 8/1966 | Stachiw | 220/46 |
| 3,353,538 | 11/1967 | Carrigan | 604/352 |
| 3,450,450 | 6/1969 | Hopkins et al. | 312/1 |
| 3,477,424 | 11/1969 | Tracy | 128/66 |
| 3,875,927 | 4/1975 | Trexler | 128/1 |
| 3,918,987 | 11/1975 | Kopfer | 134/95 |
| 4,003,371 | 1/1977 | Fischer | 604/293 |
| 4,068,852 | 1/1978 | Anglade | 277/34.3 |
| 4,106,661 | 8/1978 | Hunt | 220/232 |
| 4,465,522 | 8/1984 | Taldo et al. | 128/66 |
| 4,688,585 | 8/1987 | Vetter | 134/56 |
| 4,817,651 | 4/1989 | Crisp et al. | 604/289 |

FOREIGN PATENT DOCUMENTS 8300645 3/1983 World Int. Prop. O. ............ 128/66

Primary Examiner—C. Fred Rosenbaum
Attorney, Agent, or Firm—LaValle D. Ptak

[57] ABSTRACT

An expandable cuff assembly encloses a circular opening in the front panel of a lavage machine. The opening is made large enought to permit arms of a user to be inserted freely through the opening. After this is done, the expandable cuff member is filled with air to cause it to expands from a first state, having an enlarged opening through it, to a second state where it resiliently closes against the arm of the user to prevent liquid from splashing out of the lavage machine during use. After the operation of the machine is completed, the expandable cuff member returns to its first state, with a large opening therethrough to permit withdrawal of the arms of the user freely through the enlarged opening.

22 Claims, 3 Drawing Sheets

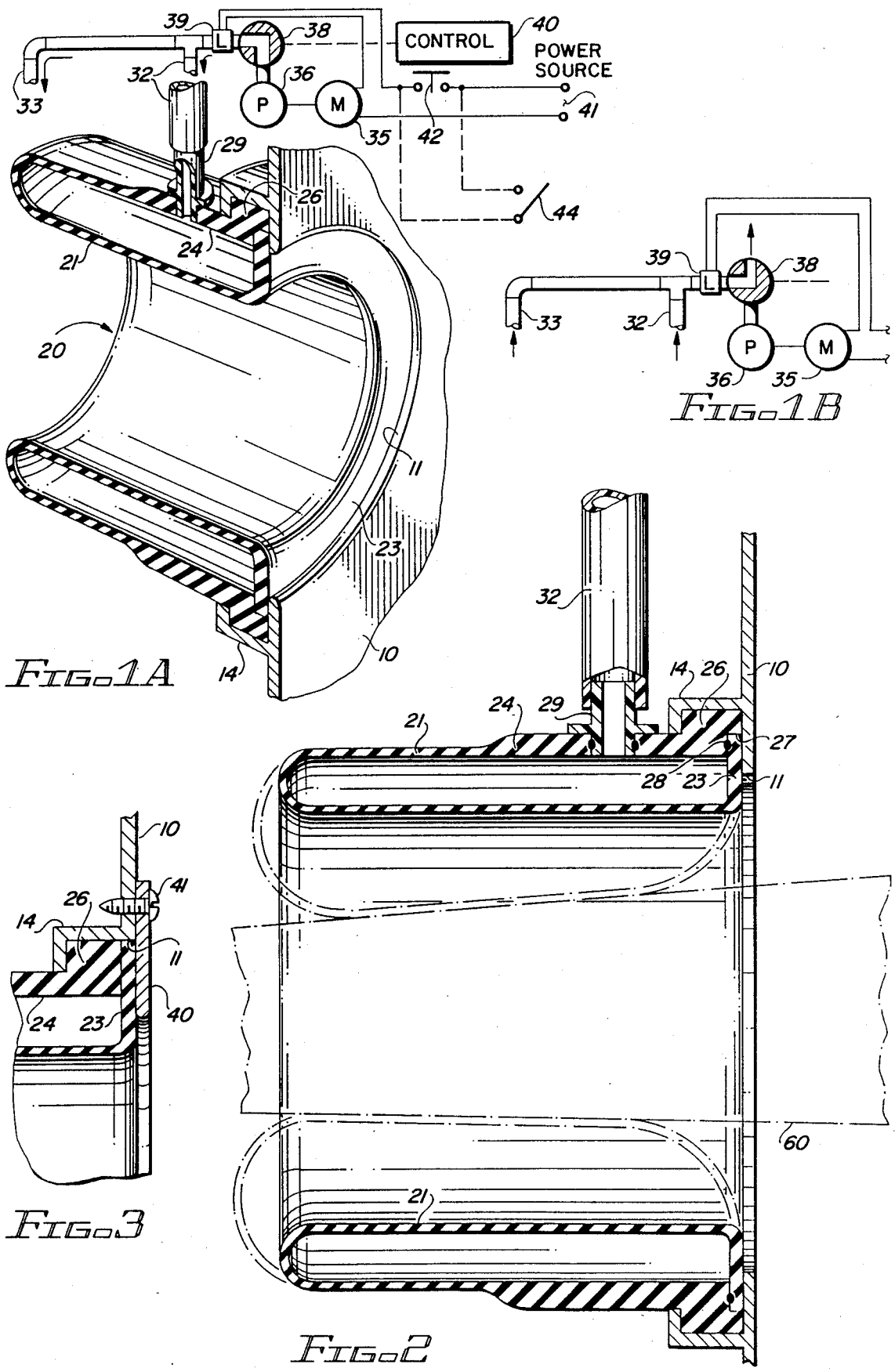

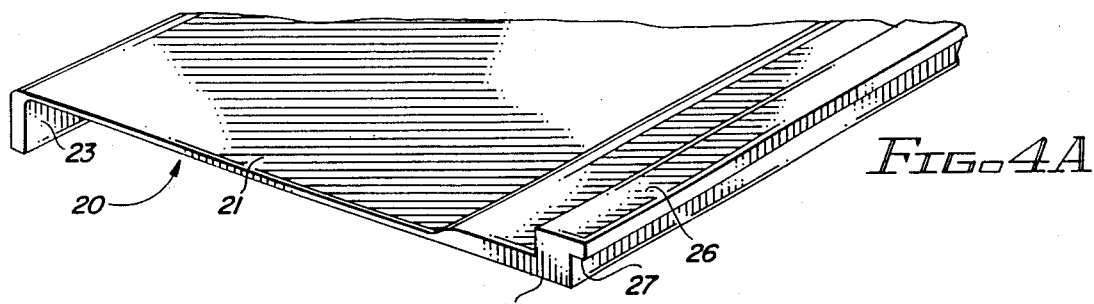
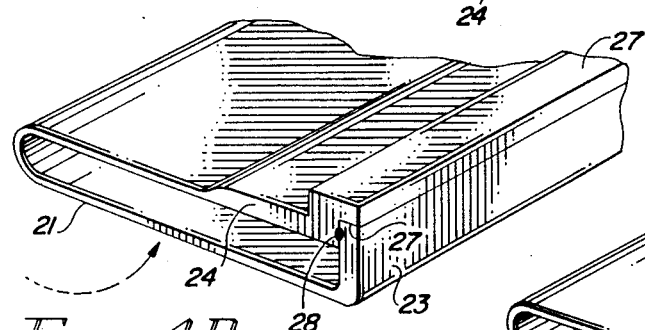
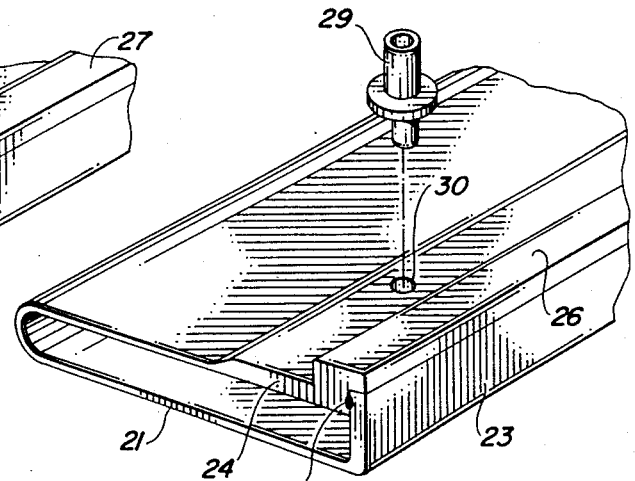
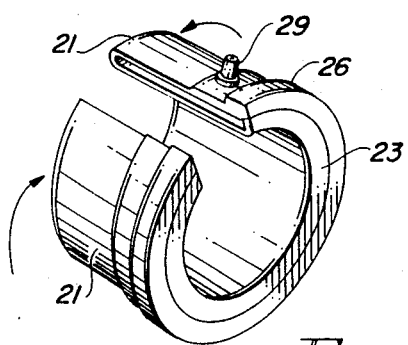
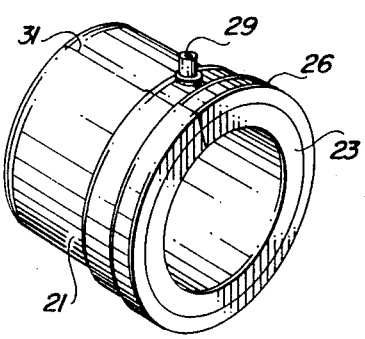
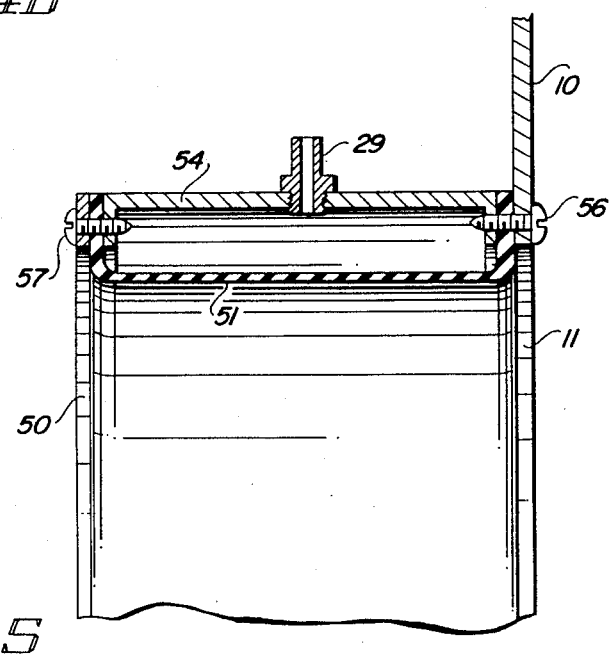

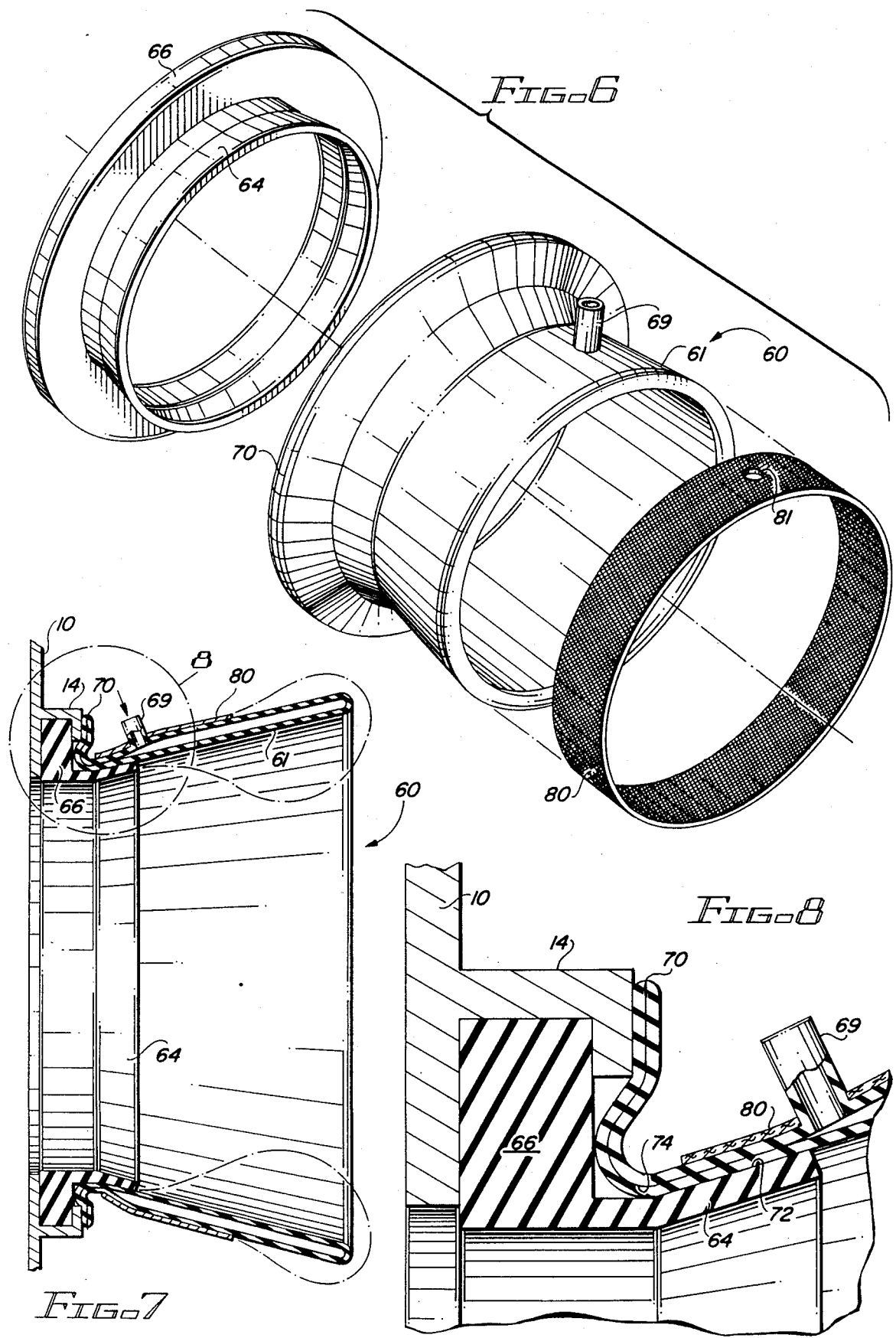

EXPANDABLE CUFF ASSEMBLY FOR LAVAGE MACHINES

BACKGROUND

Automatic washers for cleaning the hands and arms of personnel such as doctors, nurses, and restaurant workers, have been developed. Such washers are known as lavage machines. These machines typically include an arrangement of nozzles, within a sealed cabinet for directing a pressurized mixture of water, cleaning solution and anti-microbial agent onto the arms and hands inserted into the machine. The particular cleaning solution which is used varies in accordance with the application, and such machines range from relatively simple devices to multiple cycle machines incorporating washing cycles, rinsing cycles and drying cycles.

One problem which exists with such machines is in the area of the entry holes or apertures through which the hands and arms of the user are inserted. Obviously, openings of sufficient size to permit the insertion of hands and arms are necessary in the front or top panel of such a machine. When the machine is operating, in either a washing or rinsing cycle, a substantial amount of liquid is splashed around within the machine. It is desirable to prevent this liquid from splashing out through the openings around the arms of the person using the machine. Since these machines also are used to produce a germ free or bacteria free cleansing of the hands and arms, the opening must be large enough; so that the clean and sterilized hands and arms can be withdrawn from the machine without touching the edge of the opening, which typically is not free of germs and bacteria.

A lavage machine which has been designed to prevent the cleaning solution and water within the machine from splashing out of the machine is disclosed in the patent to Vetter #4,688,585. This machine has two generally circular openings for insertion of the arms of the user into the machine. Each of these openings is surrounded with an elongated elastic sleeve attached around the opening and which extends into the machine. The sleeve presses against the arm of the person using the machine, and pressurized air is applied to the machine interior further to press the elastic material of the sleeve onto the arm. As a result, when the machine is operated to clean the hands of the person using it, an effective water tight seal is formed around the arms of the person to prevent water from splashing out through the openings. A difficulty arises in this machine, however, since upon withdrawal of the arms, the hands can come into contact with the sleeve (which presses against a portion of the arm not cleaned within the machine) and thus can become contaminated. As a result, the sleeve performs the function of preventing liquid from splashing out of the machine but also is capable of recontaminating the hands of the user immediately following cleansing and sterilization. This is a serious disadvantage of the device disclosed in this patent.

Another patent disclosing a lavage machine for hand and arm washing machine is the patent to Kopfer #3,918,987. In this patent, there is no seal whatsoever in the opening into which the arm is inserted, so that some fluid can splash out through the space between the arm and the edges of the opening during the operation of the machine.

A device for providing a pressure resisting seal for a variety of purposes, such as respirators, is disclosed in the Patent to Hopkins #3,450,450. The structure of this patent has a plurality of flexible closure members attached side-by-side around an aperture in the enclosure to press against an object inserted through the closure members. Essentially they extend to fill the space in the aperture completely and are displaced when an object such an arm, torso or the like is inserted through them. Pressurized air within the enclosure then presses the members against an object inserted through the aperture to prevent the pressurized air within the device from passing outwardly. It is readily apparent, however, from an examination of the various structures disclosed in this patent, that upon removal of the object from the device, contact is made with the closure members. Thus, these structures are not suitable for use in a lavage machine where the cleansed and sterilized arm and hand must be withdrawn without coming into contact with any contaminated surface.

Four patents which disclose flexible, inflatable seals for sealing doors or lids against a frame or a container, are the patents to Reeves #2,785,824; Clark #3,178,779; Stachiw #3,266,657 and Hunt #4,106,661. In all of these patents, an inflatable seal surrounds the opening between a door or lid and a frame or container. When the door or lid is closed, the seal is inflated to expand into the space between the door or lid and the container or frame with which it is used, thereby tightly sealing the opening. The distance that the inflatable seal moves is relatively small in all of the devices disclosed in these patents, since the covers or doors close the openings within relatively close tolerances. Consequently, only a slight movement of the seal or a slight expansion of it is sufficient to securely close the opening and seal it off. None of the devices of these patents are lavage machines or hand washing machines.

It is desirable to provide a closure for the hand and arm entry openings in a lavage machine which effectively prevents liquid from splashing out of the machine during the washing operation and which also is withdrawn or pulled away from the opening a sufficient amount to permit withdrawal of the clean arms and hands from the machine without touching the closure or the opening following the washing cycle. It further is desirable to provide such a device which is capable of quickly and effectively accomplishing this purpose with persons having differing physical measurements.

SUMMARY OF THE INVENTION

Accordingly, it is an object of this invention to provide an improved closure for sealing an opening in a cabinet against an object inserted through the opening.

It is an additional object of this invention to provide an improved seal for the opening in a lavage machine.

It is another object of this invention to provide an improved expandable cuff assembly for the opening in a lavage machine.

It is a further object of this invention to provide a self-draining cuff assembly for the opening in a lavage machine.

It is yet another object of this invention to provide an expandable cuff assembly for the opening in a lavage machine for sealing the opening against the arm of a user during the washing cycle of the machine and further for permitting unobstructed removal of the arm and hand of the user of the machine following the washing cycle.

In accordance with a preferred embodiment of this invention, an expandable cuff assembly for closing an opening in a panel against an object includes an expandable cuff member formed at least in part of resilient material for mounting about the periphery of the opening through the panel. In a first state, the cuff member provides an enlarged opening through the panel for ready insertion of an object through the opening. In a second state, the cuff member expands to substantially restrict the opening and to conform against the object inserted through the opening to provide an effective seal of the opening against objects of varying sizes inserted through it. A control is provided to selectively cause the cuff member to attain the first and second states.

BRIEF DESCRIPTION OF THE DRAWINGS

FIG. 1A is a sectionalized, perspective view of a preferred embodiment of the invention, illustrating a control system in a first operating condition;

FIG. 1B illustrates a portion of the control system of the embodiment of FIG. 1A in a second condition of operation;

FIG. 2 is a cross-sectional view of the embodiment of FIG. 1A illustrating first and second states of operation;

FIG. 3 is an alternative structure of a portion of the embodiment shown in FIGS. 1A and 2;

FIGS. 4A through 4E illustrate the manner of construction of a portion of the embodiment shown in FIGS. 1A and 2;

FIG. 5 illustrates a cross-sectional view of a portion of an alternative embodiment of the invention;

FIG. 6 is an exploded perspective view of another preferred embodiment of the invention;

FIG. 7 is a cross-sectional view of the embodiment of FIG. 6; and

FIG. 8 is an enlarged detail of a portion of FIG. 7.

DETAILED DESCRIPTION

Reference now should be made to the drawings in which the same reference numbers are used throughout the difference figures to designate the same components. The embodiments of the invention which are disclosed are for use in the arm insertion openings of a hand washing machine or lavage machine of the type shown, for example, in the Patent to Vetter, discussed above.

The invention as shown in the embodiment of FIGS. 1 through 4 is an inflatable cuff for sealing the arm openings in the front of a lavage machine against the arms of the user when the machine is operated to clean the hands and/or forearms of a person. Following the cleaning operation, the cuff assembly operates to enlarge the opening to permit free removal of the hands and arms of the user from the machine without touching the cuff or opening in the machine.

The structure of the cuff member itself is illustrated in FIGS. 4A through 4E, and reference first should be made to those figures. The cuff member may be made from an elongated neoprene extrusion or elastomeric material having a relatively thin central portion 21 with a downwardly turned thickened rib 23 at one end (the left-hand end shown in FIG. 4A) and a thickened portion 24 at the right-hand end, with an upward extension 26 to form a shoulder 27 between the extension 26 and the thickened portion 24. Since this extrusion has a uniform cross-section throughout its length, the cuff 20 simply is formed from a section of a continuous extrusion. The length of the section depends upon the final diameter of the opening in which the cuff member is to be placed.

After a fixed length of the extrusion shown in FIG. 4A is cut, the material is folded back on itself by pulling the edge 23 underneath the edge 24, as illustrated in FIG. 4B, to abut the shoulder 27. A continuous bead of glue 28 may be placed along these abutting edges to form an airtight seal between them. Alternatively, thermal bonding may be employed, if desired. The result is an elongated open ended, folder over section as illustrated in FIGS. 4B and 4C. It should be noted that the relatively thin portion 21 extends from side-to-side across the bottom of this subassembly and substantially half of the length on the upper side, extending to the left of the thickened section 24, as illustrated in FIGS. 4A and 4B.

A hole 30 then is formed through the thickened portion 24, and an air hose stem 29 is inserted into the hole 30 and is glued to or otherwise bonded to the portion 24 to form an airtight seal. The lower end of the stem 29 extends into the interior of the envelope formed by the folded-over portion 21, as illustrated most clearly in FIGS. 1A and 2.

After the device has been assembled in its flat form shown in FIGS. 4A and 4B, it is rolled up as illustrated in FIG. 4D; and the opposite edges are bonded together along the bond line 31 to form an airtight envelope within the interior of the folded over portion 21. This is illustrated in FIG. 4E. The assembly of FIG. 4E then comprises a hollow cuff member which is secured into an opening 11 of the front panel 10 of a lavage machine.

When the cuff member is configured as illustrated in FIGS. 4A through 4E, the relatively rigid thickened extension 26 snap fits into a channel 14 formed behind the opening 11 in the front face of the panel 10, as illustrated most clearly in FIGS. 1A and 2. This causes the edge 23 to extend upwardly behind the lower edge of the panel 10 at the opening 11. The dimensions of the channel 14 are made to cause this to be a relatively tight fit. Because of the nature of the extrusion, the rolled cuff member of FIG. 4E tends to press outwardly into the channel 14, so that it is held securely in place behind the front panel 10 once it has been snapped into the channel 14. There is sufficient resiliency in the stiffened portions 24, 26 and 23 to permit installation of the assembly in the channel 14 simply by "popping" it into place, as illustrated in FIGS. 1A and 2.

After the cuff member 20 has been inserted into the channel 14, an air pipe 32 for one opening 11 or 33 for the other opening (not shown) in the panel 10 of the lavage machine is connected to the stem 29. This permits the supply of air into and the removal of air from the enclosed cavity formed within the cuff member 20 between the folded over portions 21, forming the outer and inner sides of the elongated annular sleeve of the cuff assembly.

Typical dimensions for the cuff assembly and the lavage machine opening are for the opening 11 to be approximately five (5) inches in diameter for wrist sealing and six (6) inches for arm sealing. This permits ready passage of the hand and forearm of a user of the machine through the opening with adequate clearance. The depth of the member 20 from right to left, as viewed in FIGS. 1A and 2, is approximately four (4) inches. The relaxed thickness of the member 20 (when air pressure has been removed from it), as illustrated in FIGS. 1A and 2 in solid lines, is approximately one-half inch from the outer surface to the inner surface. The channel 14 is approximately one-half inch wide; and the depth of the channel 14 from the portion which touches the upper surface of the extension 26 to the edge of the opening 11 is approximately one inch. Also, as illustrated most clearly in FIG. 2, the relatively rigid thickened portion 24 extends approximately one-half of the front to back distance of the cuff member 20.

When the device is in its relaxed state, as illustrated in FIGS. 1A and 2, the rigidity of the portion 24 causes it to assume the configuration shown in solid lines in FIG. 2. This provides easy access for insertion of the forearm 60 of a person using the device through the opening 11 in the front panel 10. A system is provided for pumping air under pressure into the envelope within the walls 21 to expand the flexible walls 21 on the inside of the device from the solid line position to the dotted line position shown in FIG. 2. To accomplish this, a motor 35 is used to drive a pump 36 to supply air through a valve 38 (in the position shown in FIG. 1A) through a pressure limit switch 39 into the supply pipe 32 (and 33). The pipe 32 then supplies air through the stem 29 to increase the pressure within the envelope 21 of the cuff member 20. The wall portion 21 is relatively thin; and since the inner surface is made entirely of this thin wall section, the portion 21 resiliently stretches downwardly to the dotted line configuration of FIG. 2. This forms an annular air-filled ring, the inside surface of which expands to substantially restrict the size of the opening.

When the inner surface 21 of the cuff member engages the forearm of a person using the machine it firmly and gently presses against the forearm 60 on all sides to securely seal the opening against the arm. As illustrated in FIG. 2, the resiliency of the portion 21 causes the cuff member to conform to the shape of the arm 60 and the angle at which it is inserted into the machine; so that arms of different sizes, and entering the opening 11 at different angles, all are accomodated with a secure seal. It has been found that an air pressure of approximately one to five pounds per square inch is sufficient when the wall thickness 21 of the sleeve is approximately 0.025 to 0.040 inches thick.

The time at which the motor 35 is turned on is determined by operation of a switch 42 in conjunction with the operating cycle of the lavage machine. This can be affected automatically or manually to supply power from a suitable power source 41 to operate the motor 35 and to control the limit switch 39. A control device 40, also part of the lavage machine, is used to operate the valve 38 to the position shown in FIG. 1A when air is to be supplied through the stem 29 into the interior of the cuff to expand it, as shown in dotted lines in FIG. 2.

Upon completion of a washing cycle, the switch 42 is opened, and the control device 40 rotates the valve 38 to the position shown in FIG. 1B. This permits the natural resiliency of the cuff member 20 to expel air through the valve 38 into the surrounding room as the cuff member resumes its original shape, as shown in solid lines in FIGS. 1A and 2. If desired, the motor 35 and pump 36 can be operated to evacuate air through the valve 38 by interconnecting these elements through suitable conduits and additional valves. It has been found, however, that the cuff, having the characteristics and dimensions described above, has sufficient "memory" to quickly and effectively expel the air when the valve 38 is opened, as shown in FIG. 1B. Thus, evacuation of the air by a pump usually is not necessary.

FIG. 1A also illustrates an optional second switch 44 for operating the motor 35, since a variety of control sequences may be used in various lavage machines for causing the operation to take place. Once the internal surface 21 of the cuff member engages the arm of a user, pressure builds up relatively rapidly within the cuff member; and a pressure limiting switch 39 may be employed to prevent excess pressure from occurring. The switch 39 is set to operate when a desired maximum pressure is reached. Upon occurance of this pressure, the switch 39 functions to open the circuit to the motor 35 to turn off the pump 36. This provides an accurate control point for determining that the cuff member 20 has, in fact, closed the opening around the arm 60 of the user, since the amount of air delivered into the cuff member 20 varies, depending upon the size of the arm 60 of the person using the machine.

FIG. 3 illustrates an alternative construction for the cuff member and the channel 14 which may be used in place of the one shown in FIGS. 1A and 2, if desired. In the device shown in FIG. 3 a channel 14' is formed as an extension of the panel 12 inwardly from the edge of the opening 11. The cuff assembly is formed in the same manner described in conjunction with FIGS. 4A through 4E, except that the shoulder 27 may be eliminated and the edge 23 is extended parallel to the upper edge of the extension 26. An annular ring 40 then is secured by means of a series of screws or other fasteners 41 around the edge of the opening to firmly clamp the edge 23 and the portion 26 together against the left hand edge of the channel 14', as illustrated in FIG. 3. In all other respects, the construction of the device made in this manner is the same as the embodiment described above in conjunction with FIGS. 1A, 2 and 4.

FIG. 5 shows another variation of the invention which may be employed, if desired. In the embodiment of FIG. 5, the expandable or inflatable cuff member simply is in the form of a flat sheet 51 of neoprene. This sheet is rolled and joined at its edges to form an elongated cylindrical sleeve. The material 51 is of uniform thickness throughout its length or may include thickened edges similar to the edge 23, if desired. It should be noted, however, that in the embodiment of FIG. 5 the sleeve is not an enclosed balloon or tube-like member, but simply is a cylindrical member with upturned or outwardly turned edges. The channel 14 then is replaced with an elongated U-shaped channel 54, extending from the inside of the panel 10 to the interior of the lavage machine the full depth of the member 51. Thus, the channel 54 is approximately five (5) inches or six (6) inches wide in contrast to the approximately one inch width of the channel 14 of the embodiment of FIGS. 1A and 2. The stem 29 is inserted through the channel 54, as illustrated in FIG. 5.

The assembly of FIG. 5 is completed by means of threaded fasteners 56 placed about the periphery of the opening 11 in the panel 10 and extending through the upwardly turned edge of the sleeve 51 into the downwardly turned right-hand flange on the channel 59. An annular ring 50 (similar to the ring 40 of FIG. 3) is provided on the inside of the assembly and is secured to the other flange of the channel 54 by means of threaded fasteners 57 about the periphery. When the fasteners 56 and 57 are secured around the annular openings formed at each end of the channel 54, an air tight seal is formed between the channel 54 and the member 51. The member 51 may be inflated and deflated in the same manner described above in conjunction with the operation of the system of FIGS. 1A and 2. It should be noted, however, that because the member 51 is securely held at both ends, the central portion expands inwardly to the greatest amount, so that the contact with the arm of a user inserted through the opening 11 is a narrower region of contact than it is with the device of FIGS. 1A and 2. In all other respects, however, the cuff member of FIG. 5 operates in a manner similar to the cuff member of the embodiment of FIGS. 1A and 2.

Reference now should be made to FIGS. 6, 7 and 8 which illustrate another preferred embodiment of the invention directed to a cuff member which is made of a molded elastomer, such as rubber, instead of the extrusion construction which is shown in the embodiments of FIGS. 1 through 5. In the embodiment shown in FIGS. 6 through 8, a cuff 60 is made as a unitary molded element by dipping a preformed mold (not shown) into a liquid elastomer, such as rubber latex or the like, one or more times to obtain the desired wall thickness for the cuff. The overall shape of the cuff is established by the shape of the mold to produce an outwardly flaring frusto-conical shape to the finished product. The mold is completely immersed to form a hollow, completely enclosed structure. To remove the finished cuff 60 from the mold, a circular cut 70 is made around the periphery of an outwardly extending flange, shown most clearly in FIG. 6. Once this cut has been made all of the way around the mold, the molded cuff member 60 may be stripped from the mold and then returned to its original shape as illustrated in FIG. 6.

A second part of the cuff assembly of the embodiment of FIGS. 6 through 8 is in the form of a relatively thick molded elastomer ring 66 having a inwardly extending flange 64 on it. This ring 66 is comparable to the thickened portion or upward extension 26 of the embodiment shown in FIGS. 1 through 5.

To assemble the embodiment of FIG. 2, a suitable adhesive is placed on the outer surface of the flange 64 on the ring 66 to secure the inner edge of the conical sleeve 61 of the cuff 60 to the flange 64 in an airtight and watertight relationship. Similarly the inner surfaces of the cuff 60 along the cut 70 and extending around the flange 64 are also secured together with a suitable adhesive to form an airtight seal.

When the device is thus assembled, it then snap fits into the channel 14 formed behind the opening 11 in the front face of the panel 10 of the lavage machine. This is shown most clearly in FIGS. 7 and 8. It should be noted that the inner downwardly turned flange of the channel 14 extends between the upward edges of the outwardly turned portion of the cuff 60 adjacent the cut line 70.

It also is possible, however, to configure the channel 14 in a way to cause the inner flange to overlie the opposite side of the outwardly turned portion of the sleeve member 60, so that the cut line 70 and the adjacent portions of the adhesively secured together flange member, all are located within the channel 14. In either event, the operation of the cuff 60 is the same; and it should be noted that the assembly is held securely in place behind the front panel 10 of the lavage machine once it is snapped into place. This permits easy replacement of the cuff 60 in the event it should become damaged or worn out. The existing worn cuff 60 and its assembled ring 66 is simply pulled out of the channel 14 and a new one is pressed into place.

The air hose nipple 69 of the embodiment shown in FIGS. 6 through 8 also is molded into the assembly as a part of the original mold. The closed end then is cut off and a rigid connector (not shown) for attachment to the supply pipe 32 or 33 is inserted.

In operation, the embodiment of FIGS. 6 through 8 functions much in the same manner as the embodiments of FIGS. 1 through 5. When the machine is to be used, air is introduced into the hollow interior of the cuff 60 through the air hose nipple 69. This air is supplied at a pressure of approximately one to five pounds per square inch and inflats the region between the inner and outer surfaces 61 to expand this region much in the order of an expanding balloon. To focus the expansion on the inside surface, which causes the cuff to engage the arm or wrist of the user, a non-expandable ring 80 is placed over the cuff portion 60, with the air hose nipple 69 extending through a hole 81 in the ring 80. The ring 80 may be made of any suitable plastic material in the form of a solid ring or a mesh-like structure. It must exhibit the characteristics of resisting expansion in the radial direction. The ring 80 may be bonded to the outer surface of the sleeve 61, if desired.

As is shown most clearly in FIG. 7, when the ring 80 is in place, the expansion of the material of the conical sleeve 61 of the cuff 60 in the outer direction is significantly inhibited by the ring 80, while the inner expansion toward the axis of the opening through the ring 66 is unrestricted. This is illustrated by the dotted lines in FIG. 7 which illustrate the expanded position of the inner and outer portions of the conical sleeve 61 of the cuff member 60. When the device is expanded to the dotted line configuration the arm or wrist of the user is engaged by the cuff to prevent cleaning solution from splashing out of the lavage machine.

Upon completion of the washing cycle, the air pressure through the nipple 69, is removed and the cuff member either is subjected to a vacuum or reverse air flow through the nipple 69 or simply is permitted to collapse to its "memory" state, which is shown in solid lines in FIG. 7. The arm and hand of the user then easily may be withdrawn through the opening in the ring 66 in the manner described previously.

The conical shape gives a type of hoop memory to the device and provides a smooth water free-surface when the cuff 60 attains its uninflated or retracted condition of operation as, shown in solid lines in FIG. 7. It can be seen that any liquid which may be present on the inside portion of the cuff will drain downwardly and outwardly to the bottom edge, where it is returned to the interior of the lavage machine. This self-draining feature is important for minimizing contamination.

It should be noted that with all of the embodiments disclosed, a substantial expansion of the cuff member from its relaxed state to its expanded state occurs. That is, the cuff member portion 21 or 51 has sufficient resiliency in the range of pressures used within the system to cause it to close the opening through the cuff member from approximately five or six inches (when the cuff member is in its relaxed state) down to approximately one inch diameter. Thus, arms of persons having considerable different physical characteristics may be accomodated within the machine.

The foregoing embodiments of the invention which have been described and which are illustrated in the drawings are to be considered illustrative of the invention and not as limiting. Various changes and modifications will occur to those skilled in the art. For example the dimensions which have been given are typical of an actual embodiment of the invention, but may be varied in accordance with different physical requirements of different lavage machine installations. Although the structure for the expandable and inflatable cuff member has been described as latex or neoprene, other rubber-like materials may be used, if desired. In addition, different configurations of the inflatable cuff also will occur to those skilled in the art without departing from the true scope of the invention.

We claim:

1. An expandable cuff assembly for closing an opening in a panel against an object inserted through such opening, said assembly including in combination:
   an expandable cuff member, formed at least in part of resilient material, and made from an elongated section of unitary material folded back on itself in a longitudinal direction to seal the opposite edges together forming a pocket between the folded over edges, with said cuff member further being rolled into a cylindrical configuration with the opposite ends thereof joined together to form an enclosed air pocket therein and one edge thereof attached to the periphery of an opening through a panel, said cuff member having a first state providing an enlarged opening therethrough and a second state in which the resilient material presses against objects of various sizes and shapes inserted through the opening, substantially restricting and sealing the opening therethrough as contrasted with said enlarged opening;
   control means coupled to said cuff member for selectively causing said cuff member to attain said first and second states thereof; and
   means for actuating said control means.

2. The combination according to claim 1 wherein the opening in the panel is a circular opening and said expandable cuff member is an elongated cylindrical ring-like member mounted in said opening for expansion from said first state, with a relatively large circular opening therethrough, to a second state with a substantially smaller opening therethrough.

3. The combination according to claim 2 wherein at least said part of said cuff member formed of resilient material conforms to the shape of an object inserted through the opening in the panel for sealing said cuff member against said object.

4. The combination according to claim 3 wherein said cuff member is hollow and made of air tight material, with said control means supplying air into said cuff member to expand the resilient portion thereof from said first state to a second state, and for removing air therefrom to collapse said cuff member from said second state to said first state thereof.

5. The combination according to claim 4 wherein said control means comprises an air pump and a valve for supplying air to and removing air from said cuff member in accordance with the selective state of operation of said control means.

6. The combination according to claim 5 further including a flange encircling the opening in the panel, with said cuff member having a relatively rigid circular rim thereon for frictional insertion into said flange to mount and attach said cuff member about the periphery of the opening in the panel.

7. The combination according to claim 6 wherein at least the expandable portion of said cuff member is fabricated from a single piece of homogeneous material.

8. The combination according to claim 7 wherein said cuff member is made of elastomeric material.

9. The combination according to claim 8 wherein said expandable cuff member expands uniformly about the opening in the panel toward the center of the opening, the enlarged opening of said cuff in said first state being sufficient to admit the arm of a person.

10. The combination according to claim 9 wherein said control means further includes pressure limit switch means for limiting the pressure of air within said cuff member when said cuff member is expanded to said second state thereof.

11. The combination according to claim 1 further including a flange encircling the opening in the panel, with said cuff member having a relatively rigid circular rim thereon for frictional insertion into said flange to mount and attach said cuff member about the periphery of the opening in the panel.

12. The combination according to claim 11 wherein said cuff member is fabricated from a single piece of homogeneous material.

13. The combination according to claim 12 wherein said cuff member is made of elastomeric material.

14. An expandable cuff assembly for closing an opening in a panel against an object inserted through such opening, said assembly including in combination:
    an expandable cuff member made from molded resilient elastomeric material in a frustro-conical configuration secured in the periphery of an opening through a panel, said cuff member having a first state providing an enlarged opening therethrough and a second state in which the resilient material thereof presses against objects of various sizes and shapes inserted through the opening, substantially restricting and sealing the opening therethrough as contrasted with said enlarged opening, the frustro-conical configuration of said cuff member causing draining of fluid from the interior thereof in the first state thereof;
    control means coupled to said cuff member for selectively causing said cuff member to attain said first and second states thereof; and
    means for actuating said control means.

15. The combination according to claim 14 wherein said cuff member is hollow and made of air tight material, with said control means supplying air into said cuff member to expand the resilient portion thereof from said first state to a second state, and for removing air therefrom to collapse said cuff member from said second state to said first state thereof.

16. The combination according to claim 15 wherein said control means comprises an air pump and a valve for supplying air to and removing air from said cuff member in accordance with the selective state of operation of said control means.

17. The combination according to claim 16 wherein the enlarged opening of said cuff in said first state is sufficient to admit the arm of a person and said control means further includes pressure limit switch means for limiting the pressure of air within said cuff member when said cuff member is expanded to said second state thereof.

18. The combination according to claim 17 wherein at least said part of said cuff member formed of resilient material conforms to the shape of an object inserted through the opening in the panel for sealing said cuff member against said object.

19. The combination according to claim 18 wherein said expandable cuff member expands uniformly about the opening in the panel toward the center of the opening.

20. The combination according to claim 14 wherein said expandable cuff member expands uniformly about the opening in the panel toward the center of the opening.

21. The combination according to claim 20 wherein said cuff member is hollow and made of air tight material, with said control means supplying air into said cuff member to expand the resilient portion thereof from said first state to a second state, and for removing air therefrom to collapse said cuff member from said second state to said first state thereof.

22. The combination according to claim 21 wherein said control means comprises an air pump and a valve for supplying air to and removing air from said cuff member in accordance with the selective state of operation of said control means.

* * * * *